US00PP28121P3

(12) United States Plant Patent
Danziger

(10) Patent No.: US PP28,121 P3
(45) Date of Patent: Jun. 13, 2017

(54) ***SALVIA* PLANT NAMED 'DSALDPOCN'**

(50) Latin Name: *Salvia farinacea*
Varietal Denomination: DSALDPOCN

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 71 days.

(21) Appl. No.: 14/545,104

(22) Filed: Mar. 27, 2015

(65) Prior Publication Data

US 2016/0286708 P1 Sep. 29, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

U.S. PATENT DOCUMENTS

PP19,788 P2 * 3/2009 Danziger ..... Plt./475

OTHER PUBLICATIONS

CPVO Community Plant Variety Office Mar. 2015, retrieved on Aug. 9, 2016, retrieved from the Internet at <http://www.cpvo.europa.eu/documents/gazettes/2015/cpvo_2015_3.pdf> p. 56.*
Faribault Growers, Inc. 2015 Order Form retrieved on Aug. 9, 2016, retrieved from the Internet at <http://www.fgimn.com/2015OrderForm.pdf> pp. 1-4.*
Beytes et al. Grower Talks Good . . . and Plenty 2014 retrieved on Aug. 9, 2016, retrieved from the Internet at <http://ballpublishing.com/GrowerTalks/ViewArticle.aspx?articleid=20874> pp. 1-8.*
Proven Winners Customer—Grower Agreement, retrieved on Aug. 9, 2016, retrieved from the internet at <https://www.provenwinners.com/sites/provenwinners.com/files/pdf/customer_-_grower_agreement_exhibit_a_2013-2014_-_canada_final.pdf> 8 pp.*

* cited by examiner

*Primary Examiner* — June Hwu
(74) *Attorney, Agent, or Firm* — Cassandra Bright

(57) ABSTRACT

A new and distinct *Salvia* cultivar named 'DSALDPOCN' is disclosed, characterized by early flowering of deep blue flowers, very full and mounded habit. Additionally all the flowers are at the same height. The new variety is a *Salvia*, normally produced as an outdoor garden or container plant.

2 Drawing Sheets

Figure 1:
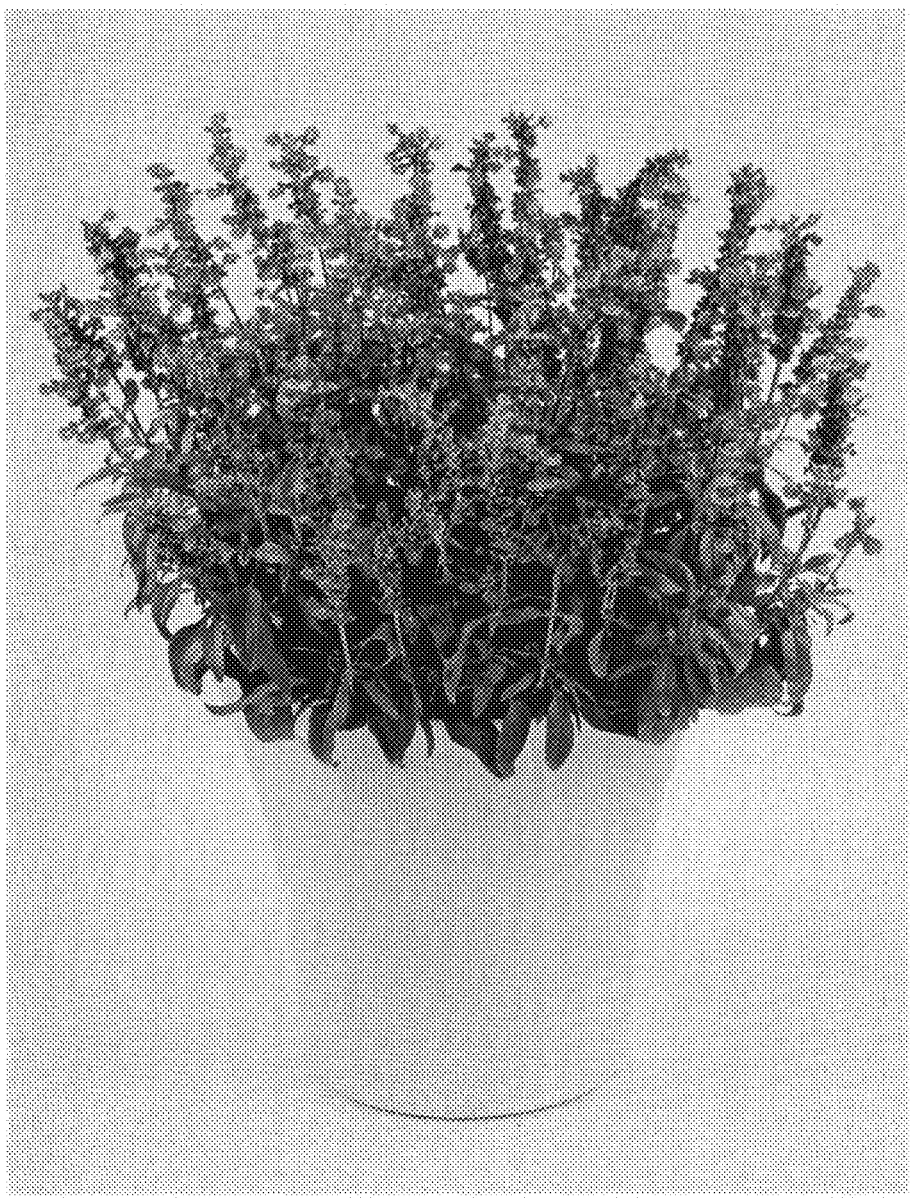

Latin name of the genus and species: *Salvia farinacea*.
Variety denomination: 'DSALDPOCN'.

BACKGROUND OF THE INVENTION

The new *Salvia* cultivar is the product of a planned breeding program conducted by the inventor, Gavriel Danziger, in Moshav Mishmar Hashiva, Israel. The objective of the breeding program was to produce new *Salvia* varieties for ornamental commercial applications. The open pollination resulting in this new variety was made during 2010.

The seed parent is the, unpatented, proprietary variety referred to as *Salvia* 'SAF-9-971'. The pollen parent is unknown as it was an open pollination breeding program. The new variety was discovered in June of 2011 by the inventor in a group of seedlings resulting from the 2010 open pollination, in a research greenhouse in Moshav Mishmar Hashiva, Israel.

Asexual reproduction of the new cultivar was performed by vegetative apical cuttings. This was first performed at a research greenhouse in Moshav Mishmar Hashiva, Israel in July of 2011 and has shown that the unique features of this cultivar are stable and reproduced true to type in multiple successive generations.

SUMMARY OF THE INVENTION

The cultivar 'DSALDPOCN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSALDPOCN' These characteristics in combination distinguish 'DSALDPOCN' as a new and distinct *Salvia* cultivar:

1. Very full and mounded plant habit.
2. Early flowering.
3. Deep blue flower color.
4. Flowers occurring at the same height Plants of the new cultivar 'DSALDPOCN' are similar to plants of the seed parent, *Salvia* 'SAF-9-971' in most horticultural characteristics, however, plants of the new cultivar 'DSALDPOCN' differ in the following;

1. Deep blue flowers. The seed parent has white flowers.
2. The new variety blooms earlier.
3. The new variety produces more flowers.
4. Shorter peduncles.

COMMERCIAL COMPARISON

Plants of the new cultivar 'DSALDPOCN' are comparable to the unpatented commercial variety *Salvia* 'Dansalfun', U.S. Plant Pat. No. 19,788. The two *Salvia* varieties are similar in most horticultural characteristics; however, the new variety 'DSALDPOCN' differs in the following:

1. The new variety has a more compact plant habit.
2. The new variety has a more full plant habit.
3. The new variety does not have noticeable white eyes on the flower, as the comparator.
4. The new variety has shorter peduncles.

Plants of the new cultivar 'DSALDPOCN' can also be comparable to the unpatented commercial variety *Salvia* 'SALLYFUN BICOLOR BEAUTY', unpatented. The two *Salvia* varieties are similar in most horticultural characteristics; however, the new variety 'DSALDPOCN' differs in the following:

1. The new variety has lower petal and upper petals the same shade of blue, whereas comparator has 2 different colors—the lower petal in shades of light blue and the upper in darker blue.
2. More compact and mounded habit. The comparator habit is more spreading.

BRIEF DESCRIPTION OF THE PHOTOGRAPHS

The accompanying photograph in FIG. 1 illustrates in full color a typical plant of 'DSALDPOCN' grown in a greenhouse, in a 13 cm pot. Age of the plant photographed is approximately 15 weeks from a rooted cutting.

Figure 2:
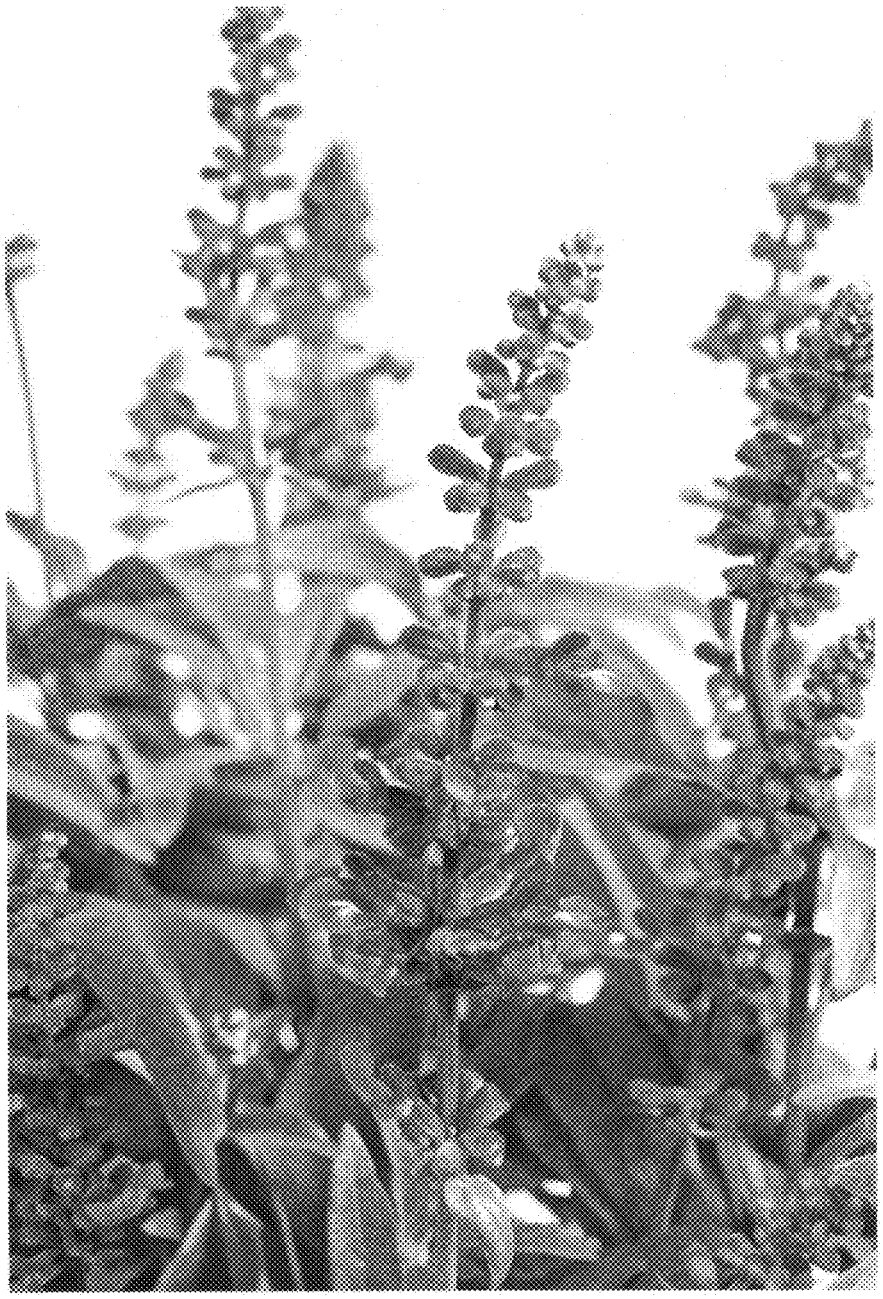

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DSALDPOCN' plants grown in the Autumn, to Spring in moderate climate in a greenhouse, in Moshav Mishmar Hashiva, Israel. The growing temperature ranged from 20° C. to 30° C. during the day and from 16° C. to 25° C. during the night. General light conditions are bright, normal sunlight. Measurements and numerical values represent averages of typical plant types.

Botanical classification: *Salvia farinacea* 'DSALDPOCN'.

PROPAGATION

Type of propagation typically used: Vegetative cutting.
Time to initiate roots: 5-7 days at approximately 25° C.
Time to produce a rooted cutting: About 10-14 days at 25° C.

PLANT

Age of plant described: Approximately 15 weeks.
Container size of the plant described: 13 cm.
Overall plant shape or growth habit: Mounded.
Length of primary lateral branches: Approximately 30 cm.
Diameter of lateral branches: Approximately 0.6 cm.
Quantity of lateral branches: About 20-25.
Branch color: Yellow-green group 144A RHS.
Branch texture/pubescence: Pulverulent, slightly ribbed longwise.
Internode length: Approximate average 2 cm.

FOLIAGE

Leaf:
- *Arrangement*.—Opposite.
- *Quantity*.—Approximately 20 per main branch.
- *Average length*.—Approximately 8 cm.
- *Average width*.—Approximately 3 cm.
- *Shape of blade*.—Ovate.
- *Apex*.—Broadly acute.
- *Base*.—Pointed.
- *Attachment*.—Petiolate.
- *Margin*.—Very slightly crenate.
- *Fragrance*.—Very minimal aromatic.
- *Texture of top surface*.—Smooth, slightly glossy, sporadically canescent.
- *Texture of bottom surface*.—Smooth, matte, sporadically canescent.
- *Color*.—Young foliage upper side: Near Yellow-green 146B RHS. Young foliage under side: Near Yellow-green 146A RHS. Mature foliage upper side: Near Yellow-green 147A RHS. Mature foliage under side: Near Yellow-green 147A RHS.
- *Venation*.—Type: Pinnate. Venation color upper side: Near Yellow-green group 146B RHS. Venation color under side: Near Yellow-green group 146C RHS.
- *Petiole*.—Average Length: Approximately 3.5 cm. Diameter: Approximately 0.2 cm. Color: Near Yellow-green group 144B RHS.

FLOWER

Natural flowering season: From early spring to late autumn in moderate climate.
Inflorescence type and habit: Bilabiate flowers arranged in vertical clusters on spike, upright.
Flower longevity on plant: About 3 to 5 days, depending on temperature.
Quantity of flowers: About 20 to 35 blooming spikes per plant.
Inflorescence size:
- *Diameter*.—Approximately 3.5 cm.
- *Height*.—Approximately 18 cm.
- *Flowers and buds per inflorescence*.—Average range 60 to 90.

Peduncle:
- *Length*.—15-18 cm.
- *Diameter*.—0.5 cm.
- *Texture*.—Pulverulent, slightly ribbed longwise.
- *Color*.—Near Violet-Blue group N92C RHS.
- *Orientation*.—About 30° from vertical.
- *Strength*.—Strong.
- *Petal arrangement*.—The corolla is sympetalous and typically bilabiate with 2 small, highly fused lobes forming an upper lip and 3 larger highly fused lobes forming a lower lip.

Individual flowers:
- *Size*.—Upper lip (tube like) Diameter: Approximately 0.3 cm. Length: Approximately 0.5 cm. Lower lip (4 fused lobe) Length: Approximately 1 cm. Width: Approximately 1.2 cm.

*Persistence*.—Non-persistent.

*Fragrance*.—Very sweet, nectar-like fragrance.

Petals: One upper lip and one lower lip with 4 lobes. Lips are fused at base. Upper lip has smooth short feather like hairs, lower lip is smooth and hairless.

*Margin*.—Slightly wavy.

*Tip shape*.—Upper lip: Rounded. Lower lip: Blunt.

*Length*.—Upper lip: 0.5 cm. Lower lip: 1 cm. Tube: 0.5 cm.

*Width*.—Upper lip: 0.3 cm. Lower lip: 1 cm. Tube: 0.3 cm.

*Texture*.—Upper lip: Upper surface: Smooth, short feather like hairs. Under surface: Glabrous. Lower lip: Upper surface: Glabrous; under surface: Glabrous. Tube: Upper surface: Glabrous; under surface: Glabrous.

Color: Upper Lip.

*When opening*.—Inner surface: Near Violet-Blue group 93A RHS. Outer surface: Near Violet-Blue group N92B RHS.

*Fully opened*.—Inner surface: Near Violet-Blue group 93A RHS. Outer surface: Near Violet-Blue group 93A RHS.

*Fading*.—Inner surface: Near Violet-Blue group 93C RHS. Outer surface: Near Violet-Blue group 93B RHS.

Color: Lower Lip.

*When opening*.—Inner surface: Near Violet-Blue group 93A RHS, streaked or blotched at base near 91D. Outer surface: Near Violet-Blue group N92B RHS, streaked or blotched at base near 91D.

*Fully opened*.—Inner surface: Near Violet-Blue group 93C RHS, streaked or blotched near base between 91D and White N155A. Outer surface: Near Violet-Blue group 93B RHS, streaked or blotched at base near White N155A.

*Aging*.—Inner surface: Near Violet-Blue group 93D RHS. Outer surface: Near Violet-Blue group 93C RHS.

Color: Tube.

*When opening*.—Inner surface: Near Violet-Blue group 91D RHS. Outer surface: Near Violet-Blue group 91A RHS.

*Fully opened*.—Inner surface: Near Violet-Blue group 92A RHS. Outer surface: Near Violet-Blue group 92C RHS.

*Fading*.—Inner surface: Near Violet-Blue group 91D RHS. Outer surface: Near Violet-Blue group 94B RHS.

Bud:

*Shape*.—Ovoid.

*Length*.—0.5 CM.

*Diameter*.—0.2 CM.

*Color*.—Near Violet-Blue group 93A RHS.

Sepals:

*Shape*.—Quantity per flower: 2 lobes fused in base to form a tube.

*Length*.—Approximately 0.6 cm.

*Width*.—Approximately 0.3 cm.

*Margin*.—Entire.

*Texture*.—Velvety, with rough lines longwise, pulverulent.

*Color*.—Near Violet-Blue group 93A RHS.

REPRODUCTIVE ORGANS

Stamens:

*Number*.—2.

*Filament length*.—Approximately 0.1 cm.

Anthers:

*Shape*.—Obovate.

*Length*.—Approximately 0.1 CM.

*Color*.—Near Greyed-Purple group N187 RHS.

*Pollen*.—Color: Near Yellow group 14A RHS. Quantity: Medium.

Pistil:

*Number*.—1.

*Length*.—Approximately 1.2 cm.

*Style*.—Length: Approximately 1 cm. Color: Near Violet group 85D RHS.

Stigma:

*Shape*.—V shape with one side longer than the other.

*Color*.—Near Violet group 85B RHS.

Ovary color: Near Green-Yellow group 1D RHS.

OTHER CHARACTERISTICS

Seeds and fruits: 1-4 seeds per flower, ovoid shape. Dark Grey-Brown in color, not accurately measured with R.H.S. chart.

Disease/pest resistance: Neither resistance nor susceptibility to normal diseases and pests of *Salvia farinacea* has been observed. Pests which can be found in *Salvia* include aphids and thrips. Typical diseases are *Peronospora lamii* and *Erysiphe cichoracearum*.

What is claimed is:

1. A new and distinct cultivar of *Salvia* plant named 'DSALDPOCN' as herein illustrated and described.

* * * * *